US009848950B2

(12) United States Patent
Hezi-Yamit et al.

(10) Patent No.: US 9,848,950 B2
(45) Date of Patent: Dec. 26, 2017

(54) METHODS AND DEVICES FOR LOCALIZED DISEASE TREATMENT BY ABLATION

(71) Applicant: MEDTRONIC ARDIAN LUXEMBOURG SARL, Luxembourg (LU)

(72) Inventors: Ayala Hezi-Yamit, Santa Rosa, CA (US); Susan Edwards, Santa Rosa, CA (US); Carol Sullivan, Santa Rosa, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 41 days.

(21) Appl. No.: 14/390,962

(22) PCT Filed: Mar. 8, 2013

(86) PCT No.: PCT/US2013/030016
§ 371 (c)(1),
(2) Date: Oct. 6, 2014

(87) PCT Pub. No.: WO2013/162722
PCT Pub. Date: Oct. 31, 2013

(65) Prior Publication Data
US 2016/0074110 A1    Mar. 17, 2016

Related U.S. Application Data

(60) Provisional application No. 61/639,798, filed on Apr. 27, 2012.

(51) Int. Cl.
*A61B 18/14*    (2006.01)
*A61N 7/02*    (2006.01)
(Continued)

(52) U.S. Cl.
CPC .......... *A61B 18/1492* (2013.01); *A61B 18/24* (2013.01); *A61N 7/02* (2013.01);
(Continued)

(58) Field of Classification Search
CPC .............. A61B 17/22004; A61B 18/02; A61B 18/1492; A61B 18/1815; A61B 18/20;
(Continued)

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| WO | WO1994007446 | 4/1994 |
| WO | WO-199525472 | 9/1995 |

(Continued)

OTHER PUBLICATIONS

Madersbacher, S. et al., "Regulation of Heat Shock Protein 27 Expression of Prostatic Cells in Response to Heat Treatment", Prostate, 1998, vol. 37: pp. 174-181.*

(Continued)

*Primary Examiner* — Michael Peffley

(57) ABSTRACT

Provided herein are methods, systems, and devices for increasing heat shock protein expression and treating conditions for which increased heat shock protein expression is expected to be beneficial using thermal ablation.

20 Claims, 9 Drawing Sheets

(51) Int. Cl.

| | | |
|---|---|---|
| *A61B 18/24* | (2006.01) | |
| *A61B 17/22* | (2006.01) | |
| *A61B 18/00* | (2006.01) | |
| *A61B 18/02* | (2006.01) | |
| *A61B 18/18* | (2006.01) | |
| *A61B 18/20* | (2006.01) | |
| *A61B 19/00* | (2006.01) | |
| *A61B 90/00* | (2016.01) | |

(52) U.S. Cl.
CPC ......... *A61B 17/22004* (2013.01); *A61B 18/02* (2013.01); *A61B 18/1815* (2013.01); *A61B 18/20* (2013.01); *A61B 19/54* (2013.01); *A61B 90/39* (2016.02); *A61B 2018/0022* (2013.01); *A61B 2018/00214* (2013.01); *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/00839* (2013.01); *A61B 2018/00863* (2013.01); *A61B 2018/0212* (2013.01); *A61B 2018/1807* (2013.01); *A61B 2018/1861* (2013.01); *A61B 2019/464* (2013.01); *A61B 2090/064* (2016.02)

(58) Field of Classification Search
CPC .......... A61B 18/24; A61B 2018/00404; A61B 2018/00434; A61B 2018/00511; A61B 2018/00577; A61B 2018/00791; A61B 2018/00839; A61B 2018/00863; A61B 2018/0212; A61B 2018/1807; A61B 2018/1861; A61B 90/39; A61B 2090/064; A61N 7/02
See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,824,005 A * | 10/1998 | Motamedi ............ A61B 18/00 600/374 |
| 5,860,974 A | 1/1999 | Abele et al. |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,562,034 B2 | 8/2002 | Edwards et al. |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto et al. |
| 6,939,346 B2 | 9/2005 | Kannenberg et al. |
| 6,949,097 B2 | 9/2005 | Stewart et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0215186 A1 | 10/2004 | Cornelius et al. |
| 2005/0059623 A1 | 3/2005 | Moonen |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |

(56) References Cited

U.S. PATENT DOCUMENTS

| | | |
|---|---|---|
| 2006/0100618 A1 | 5/2006 | Chan et al. |
| 2006/0167106 A1 | 7/2006 | Zhang et al. |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0149963 A1* | 6/2007 | Matsukuma ........... A61B 18/04 606/28 |
| 2007/0190028 A1 | 8/2007 | Qu et al. |
| 2007/0265687 A1 | 11/2007 | Deem et al. |
| 2008/0132450 A1 | 6/2008 | Lee et al. |
| 2008/0161258 A1 | 7/2008 | Henning et al. |
| 2008/0319513 A1 | 12/2008 | Pu et al. |
| 2009/0036948 A1 | 2/2009 | Levin et al. |
| 2010/0049180 A1* | 2/2010 | Wells ................... A61N 5/0616 606/12 |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0257564 A1 | 10/2011 | Demarais et al. |
| 2012/0029353 A1 | 2/2012 | Slayton et al. |
| 2012/0130289 A1 | 5/2012 | Demarais et al. |
| 2012/0130345 A1 | 5/2012 | Levin et al. |
| 2012/0172837 A1 | 7/2012 | Demarais et al. |

FOREIGN PATENT DOCUMENTS

| | | |
|---|---|---|
| WO | WO1995031142 | 11/1995 |
| WO | WO-199736548 | 10/1997 |
| WO | WO1998042403 | 10/1998 |
| WO | WO-1999/00060 | 1/1999 |
| WO | WO-200122897 | 4/2001 |
| WO | WO-200170114 | 9/2001 |
| WO | WO2003022167 | 3/2003 |
| WO | WO2003082080 | 10/2003 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO2006105121 | 10/2006 |
| WO | WO-2007008954 | 1/2007 |
| WO | WO2007078997 | 7/2007 |
| WO | WO2008049084 | 4/2008 |
| WO | WO-2013162722 | 10/2013 |

OTHER PUBLICATIONS

Sebastian P. Haen et al., "Elevated serum levels of heat shock protein 70 can be detected after radiofrequency ablation", Mar. 26, 2011, Cell Stress and Chaperones 16:495-504, DOI 10.1007/s12192-011-0261-y, available at https://www.ncbi.nlm.nih.gov/pmc/articles/PMC3156258/.*

Brundel et al., "Induction of Heat Shock Response Protects the Heart Against Atrial Fibrillation", Dec. 7, 2006, Circulation Research. 2006;99:1394-1402, available at https://doi.org/10.1161/01.RES.0000252323.83137.fe.*

David S Latchman, "Heat shock proteins and cardiac protection", Sep. 1, 2001, Cardiovasc Res (2001) 51 (4): 637-646. https://doi.org/10.1016/S0008-6363(01)00354-6.*

T. A. Mehta et al., "Heat Shock Proteins in Vascular Disease—A Review", Apr. 2005, European Journal of Vascular and Endovascular Surgery, vol. 29, Issue 4, pp. 395-402, available at http://dx.doi.org/10.1016/j.ejvs.2005.01.005.*

European Search Report for European Application No. 13159256, dated Oct. 17, 2013, 6 pages.

International Search Report and Written Opinion for International App. No. PCT/US2013/30016, dated May 13, 2013, 7 pages.

Madersbacher, S. et al. "Regulation of Heat Shock Protein 27 Expression of Prostatic Cells in Response to Hear Treatment". Prostate. 1998, vol. 37, 174-181.

U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-news—latest-news/does-renal-denervation-represent-a-new-treatment-option-for-resistant-hypertension>.

"Iberis—Renal Sympathetic Denervation System: Turning innovation into quality care." [Brochure], Terumo Europe N.V., 2013, Europe, 3 pages.

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n.l.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison Awards™ " Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

(56) References Cited

OTHER PUBLICATIONS

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot[TM] renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.

(56) References Cited

OTHER PUBLICATIONS

Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. www.time.com/time/printout/0,8816,2103278,00.html.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, The American Physiological Society 1983, pp. F1-F14.

(56) References Cited

OTHER PUBLICATIONS

Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.
Opposition to European Patent No. 2465470, dated Oct. 28, 2015, Date of Opposition Jul. 27, 2016, 34 pp.
Pieper, et al., "Design and Implementation of a New Computerized System for Intraoperative Cardiac Mapping" Journal of Applied Physiology, 1991, vol. 71 (4), pp. 1529-1539.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
U.S. Appl. No. 11/363,867, filed Feb. 27, 2006, 70 pp.
U.S. Appl. No. 60/813,589, filed Dec. 29, 2005, 62 pp.
U.S. Appl. No. 60/852,787, filed Oct. 18, 2006, 112 pp.
Ureter, https://en.wikipedia.org/wiki/Ureter, Jun. 2016, 6 pp.
Almeida, et al., "Molecular chaperones: Toward new therapeutic tools," Biomedicine & Pharmacotherapy, vol. 65, 2011, 5 pages.
Brundel, et al., "Induction of Heat Shock Response Protects the Heart Against Atrial Fibrillation", Circulation Research, 2006, vol. 99, pp. 1394-1402.
Edwards, et al., "PKA Phosphorylation of the small heat-shock protein Hsp20 enhances its cardioprotective effects," Biochem Soc Trans, Author manuscript, available in PMC, 2012, 9 pages.
Lu, et al., The Role of Heat Shock Protein (HSP) in Atherosclerosis: Pathophysiology and Clinical Opportunities, Current Medicinal Chemistry, vol. 17, 2010, 17 pages.

\* cited by examiner

METHODS AND DEVICES FOR LOCALIZED DISEASE TREATMENT BY ABLATION

RELATED APPLICATIONS

The present application claims priority to U.S. Provisional Patent Application No. 61/639,798, filed Apr. 27, 2012, entitled "METHODS AND DEVICES FOR LOCALIZED DISEASE TREATMENT BY THERMAL ABLATION," the disclosure of which is incorporated by reference herein in its entirety.

BACKGROUND

Heat shock proteins (HSPs) (also known as stress proteins or molecular chaperones) are an evolutionarily conserved and diverse group of molecular chaperones that are upregulated in response to cellular stressors such as oxidative stress, glucose deprivation, hyperthermia, hypothermia, infection, inflammation, dehydration, ischemia, and exposure to toxins.

HSPs may be broadly classified into five families according to their molecular mass: HSP100, HSP90, HSP70, HSP60, and small HSPs (sHSPs). sHSPs are known to be abundant in cardiac and skeletal muscle, where they increase in response to stress to protect against muscle ischemia.

The chaperone activities of HSPs include prevention of protein misfolding, refolding of denatured proteins, and targeting of proteins for proteolytic degradation. In humans, HSPs are most notably associated with the cardiovascular, renal, central nervous, lymphatic, and immune systems. In addition, there is a strong functional relationship between the sympathetic nervous system (SNS) and HSPs.

HSPs play a key role in cell survival through cytoprotective mechanisms (Almeida Biomed Pharmacother 65:239 (2011)), and are involved in responding to a variety of disease processes including those of cancer, cardiovascular disease, neurodegenerative disease, trauma, diabetes, and chronic inflammation.

DETAILED DESCRIPTION

Figure 1:
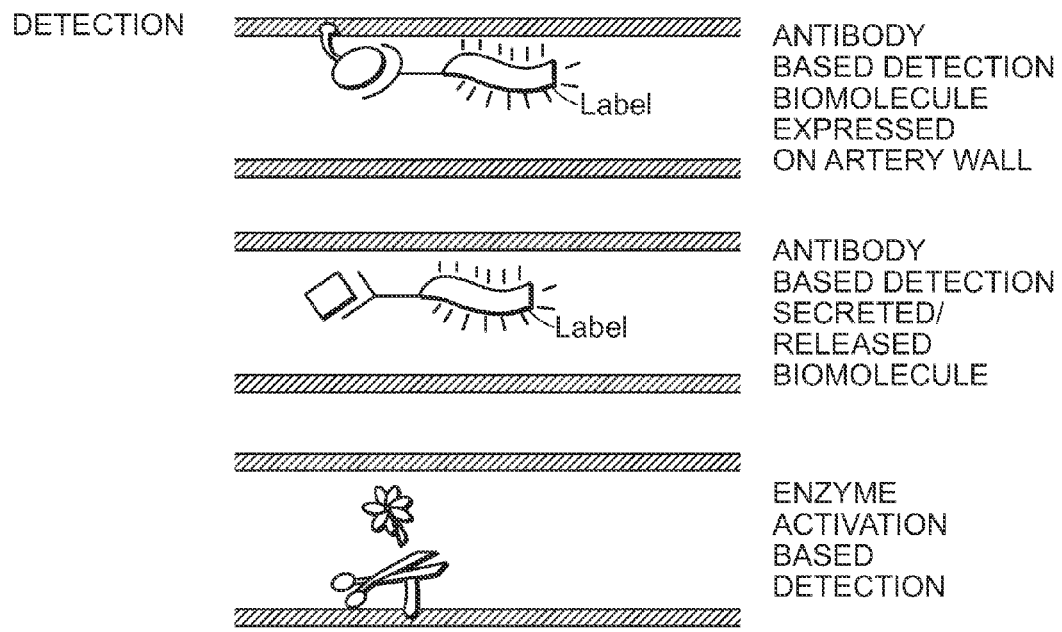
FIG. 1: Examples of HSP detection methods: antibody-based detection (upper and middle panel) and activity-based detection (lower panel).
Figure 2:
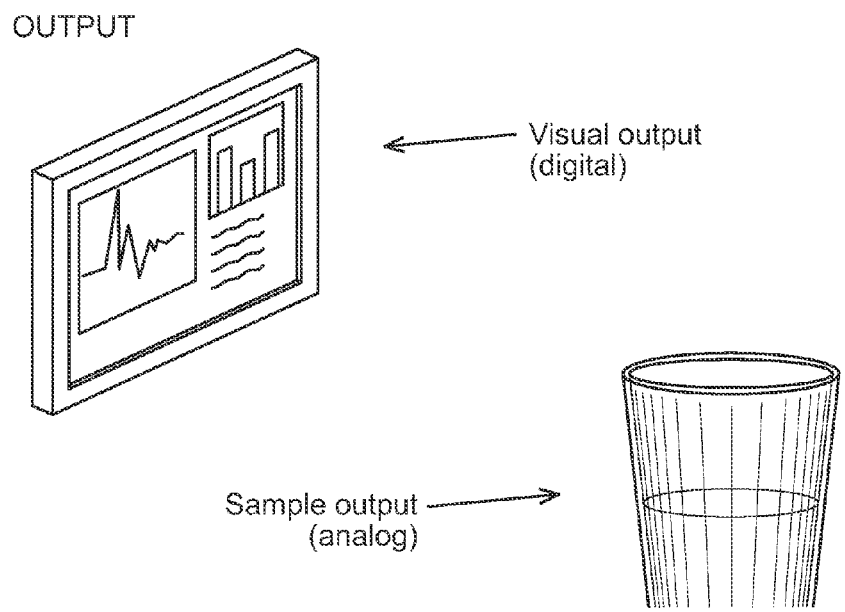
FIG. 2: Illustrative digital and analog outputs for displaying a detectable signal generated by the interaction of HSPs with a capture or detection agent.

The present technology is directed to methods, systems, devices, and kits for increasing HSP expression levels at or near a target site using ablation, as well as to methods, systems, devices, and kits for increasing local expression of HSP and treating conditions for which increased HSP levels are expected to be beneficial by increasing HSP expression. Although many of the embodiments are described with respect to methods, systems, devices, and kits for treating various conditions using thermal ablation, other applications (e.g., use of non-thermal ablative modalities) and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below.

Decreased induction of HSPs has been implicated in a variety of diseases, including cardiovascular disease (CVD) (e.g., myocardial infarction (MI) or myocardial ischemia), neurodegeneration, trauma, stroke, diabetes, atherosclerosis, chronic inflammation, cancer, and various neurological disorders. Given the key role of HSPs in cytoprotective mechanisms and the association between decreased HSP expression and various disease states, HSPs represent attractive therapeutic targets. Several attempts have been made to utilize HSPs as therapeutic agents. For example, whole-body hyperthermia (to induce the general production of endogenous HSPs) and vaccination (to introduce amounts of specific exogenous HSPs) have been used to treat conditions for which increased HSP expression is expected to be beneficial. Despite positive study results, targeted treatment has proven difficult. Thus, there is a need for new HSP treatment modalities for increasing HSP concentration in a localized manner, for example to target treatment to a specific organ or system.

Thermal ablation is frequently used to remove or inactivate a target body tissue by applying targeted heat (hyperthermal ablation) or cold (hypothermal ablation). Examples of hyperthermal ablation techniques include the use of monopolar or bipolar radio frequency (RF) energy, microwave energy, laser light or optical energy, ultrasound energy (e.g., intravascularly delivered ultrasound, extracorporeal ultrasound, high frequency ultrasound (HIFU)), magnetic energy, and direct heat energy. Examples of hypothermal ablation techniques include the use of cryotherapeutic energy. Hyperthermal ablation has been used to treat a variety of conditions, including cancer of the lung, liver, kidney, and bone, and conditions associated with electrical conduction in the heart such as arrhythmia.

Thermal ablation can also be used to partially or completely disrupt the ability of a nerve to transmit a signal. For example, intravascular devices that reduce sympathetic nerve activity by applying RF energy to a target site in the renal artery have recently been shown to reduce blood pressure in patients with treatment-resistant hypertension. The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent renin-angiotensin-aldosterone system (RAAS) activation) and sodium retention and decreased renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure).

As disclosed herein, thermal ablation of renal sympathetic nerves has been found to unexpectedly increase local expression of several HSPs. This increase was observed at 10 minutes, 24 hours, and 7 days post-ablation, indicating that HSP levels remain elevated for an extended period following ablation. Based on this finding, methods, systems, and devices are provided herein for increasing HSP expression and for treating various conditions for which increased HSP levels are expected to be beneficial.

Specific details of several embodiments of the technology are described below with reference to FIGS. 1-14. Although many of the embodiments are described below with respect to methods, systems, and devices for inducing HSP expression and treating conditions for which increased HSP expression is expected to be beneficial using thermal ablation, other applications (e.g., using other techniques such as non-thermal neuromodulation to increase HSP expression) and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-14.

Disclosed herein are several embodiments of methods for increasing HSP expression at or near a target tissue site and treating conditions for which increased HSP levels are expected to be beneficial in a subject need thereof using thermal ablation. The methods disclosed herein represent a significant improvement over conventional approaches and techniques in that they allow for more specific targeting of HSP induction and thus localized treatment. Further provided herein are systems and devices for use in conjunction with the disclosed methods.

Provided herein in certain embodiments are methods for increasing HSP expression levels at or near a target site in a subject by performing a thermal ablation procedure at or near the target site. In certain of these embodiments, HSP expression levels are increased within 30 minutes following the thermal ablation procedure, and in certain of these embodiments HSP expression levels are increased within 10 minutes following the thermal ablation procedure. In certain embodiments, HSP expression is increased at one or more specified timepoints following ablation, and in certain of these embodiments HSP expression is increased at 10 minutes, 24 hours, or 7 days following ablation. In certain embodiments, the thermal ablation procedure is carried out using monopolar or bipolar RF energy, microwave energy, laser light or optical energy, ultrasound energy (e.g., intravascularly delivered ultrasound, extracorporeal ultrasound, HIFU), magnetic energy, direct heat energy, or cryotherapeutic energy. In certain embodiments, the target site is in a renal blood vessel, and in certain of these embodiments the thermal ablation procedure targets renal sympathetic nerves.

Provided herein in certain embodiments are methods for treating conditions for which increased HSP expression is expected to be beneficial in a subject by performing a thermal ablation procedure, wherein the procedure increases HSP expression levels. In certain of these embodiments, HSP expression levels are increased within 30 minutes following the thermal ablation procedure, and in certain of these embodiments HSP expression levels are increased within 10 minutes following the thermal ablation procedure. In certain embodiments, HSP expression is increased at one or more specified timepoints following ablation, and in certain of these embodiments HSP expression is increased at 10 minutes, 24 hours, or 7 days following ablation. In certain embodiments, the thermal ablation procedure is carried out using monopolar or bipolar RF energy, microwave energy, laser light or optical energy, ultrasound energy (e.g., intravascularly delivered ultrasound, extracorporeal ultrasound, HIFU), magnetic energy, direct heat energy, or cryotherapeutic energy. In certain embodiments, the target site is in a renal blood vessel, and in certain of these embodiments the thermal ablation procedure targets renal sympathetic nerves.

Provided herein in certain embodiments are devices, systems, and kits for carrying out the methods disclosed herein.

In certain embodiments, the methods provided herein comprise performing thermal ablation, thereby increasing HSP expression at or near the target site. An increase in HSP expression may refer to an increase in mRNA or protein level for one or more HSPs or to an increase in secretion of one or more HSPs. In certain embodiments, thermal ablation results in an increase in HSP activity at or near a target site in addition to or in lieu of an increase in HSP expression. In certain embodiments, thermal ablation may be repeated one or more times at various intervals until a desired HSP expression level or another therapeutic benchmark is reached. An increase in HSP expression may be observed for a single HSP, or it may observed across a range of two or more HSPs. In certain embodiments, the methods disclosed herein result in an increase in a single specific HSP. In other embodiments, the methods disclosed herein result in an increase in expression of a subset of two or more specific HSPs, or an increase in HSP expression generally. Examples of HSPs that may exhibit increased expression in response to thermal ablation are set forth in Table 1.

TABLE 1

| Gene | Location | Gene Product Function/Description | Reference |
|---|---|---|---|
| Clusterin (CLU) | Secreted | Secreted chaperone (heatshock protein) | Lu Curr Med Chem 17: 957 (2010) |
| DnaJ (Hsp40) homolog subfamily A member 4 (DNAJA4) | Intracellular/ Surface | Protein folding and heat response | Sonna J Appl Physiol 92: 1725 (2002) |
| DnaJ (Hsp40) homolog subfamily B member 1 (DNAJB1) | Intracellular | Interacts with Hsp70, stimulates ATPase activity | Lu Curr Med Chem 17: 957 (2010) |
| Heat shock 27 kDa protein 1 (HSPB1) | Intracellular | Stress resistance, actin organization | Lu Curr Med Chem 17: 957 (2010) |
| Heat shock 60 kDa protein 1 (HSPD1) | Intracellular | Chaperonin, involved in folding of mitochondrial matrix proteins | Lu Curr Med Chem 17: 957 (2010) |
| Heat shock 105 kDa/110 kDa protein 1 (HSPH1) | Intracellular | Prevents aggregation of denatured proteins under severe stress | Lu Curr Med Chem 17: 957 (2010) |
| Heme oxygenase (decycling) 1 (HMOX1) | Intracellular | Catalyzes degradation of heme, active during physiological stress | Sonna J Appl Physiol 92: 1725 (2002) |
| Heat shock 70 kDa protein 5 (HSPA5) | Intracellular | Facilitates assembly of multimeric protein complexes in ER | SABiosciences $RT_2$ Profiler PCR Array Human Neurotoxicity platform |

In certain embodiments of the methods provided herein, thermal ablation results in an increase in HSP levels over a specific timeframe. In certain of these embodiments, HSP levels are increased over an acute timeframe, e.g., within 30 minutes or less following ablation. For example, HSP levels may be increased at 30 seconds, 1 minute, 2 minutes, 5 minutes, 10 minutes, 15 minutes, 20 minutes, or 30 minutes post-ablation. In certain embodiments, HSP levels may be elevated at one or more timepoints beyond an acute timeframe. In these embodiments, HSP levels may be elevated at or near the target site at 1 hour or more, 2 hours or more, 6 hours or more, 12 hours or more, 24 hours or more, 48 hours or more, 72 hours or more, or a week or more after the ablation procedure. In certain embodiments where HSP levels are increased over an acute timeframe, levels remain increased beyond the acute timeframe. In other embodiments, HSP levels are elevated during the acute timeframe, but drop back to a baseline level or below before the end of the acute timeframe.

In certain embodiments, the methods disclosed herein may comprise an additional step of measuring HSP expression levels, and in certain of these embodiments the methods further comprise comparing the HSP expression level to a baseline HSP expression level. Such measurements and comparisons can be used to monitor therapeutic efficacy and to determine when and if to repeat the ablation procedure. In certain embodiments, a baseline HSP expression level is derived from the subject undergoing treatment. For example, baseline HSP expression may be measured in the subject at one or more timepoints prior to thermal ablation. Baseline HSP value may represent HSP expression at a specific timepoint before thermal ablation, or it may represent an average expression level at two or more timepoints prior to thermal ablation. In certain embodiments, the baseline value is based on HSP expression at or near the target site immediately prior to thermal ablation (e.g., after the subject has already been catheterized). Alternatively, a baseline value may be derived from a standard value for HSP expression observed across the population as a whole or across a particular subpopulation. In certain embodiments, post-ablation HSP levels are measured in an acute timeframe, i.e., while the subject is still catheterized and/or under anesthesia.

In certain embodiments of the methods provided herein, the increase in HSP expression level post-ablation may result in an expression level at or near the target site that is greater (e.g., two-fold or greater, three-fold or greater, or five-fold or greater, etc.) than a baseline HSP expression level at one or more timepoints post-ablation. For example, HSP levels may be elevated to a level two-fold or greater than the baseline expression level at one or more timepoints within an acute timeframe, e.g., within 30 minutes or less following ablation.

In certain embodiments of the methods provided herein, the methods are designed to increase HSP expression to a target level. In these embodiments, the methods include a step of measuring HSP levels post-ablation and comparing the resultant expression level to a baseline expression level as discussed above. In certain of these embodiments, the ablation step is repeated until the target HSP level is reached. In other embodiments, the methods are simply designed to increase HSP above a baseline level without requiring a particular target expression level.

The methods disclosed herein result in a localized increase in HSP expression, i.e., at or near a target site. In certain embodiments, the methods may further result in an increase in HSP expression levels at locations remote to the target site. In certain of these embodiments, HSP expression levels may be elevated systemically, such that they can be detected by a urine or blood draw from a subject.

In those embodiments of the methods disclosed herein that are directed to the treatment of a condition for which increased HSP expression is expected to be beneficial, the condition may be selected from the group consisting of, for example, CVD (e.g., myocardial ischemia, acute myocardial ischemia, chronic myocardial ischemia, MI, ischemia/reperfusion (I/R) injury, peripheral artery disease (PAD)), trauma, stroke, diabetes, atherosclerosis, asthma, other chronic inflammatory conditions, cancer, neurodegeneration, and various neurological disorders. In certain embodiments, the condition may be associated with decreased levels of HSP expression. In other embodiments, the condition may not be associated with decreased levels of HSP expression, but nonetheless may be expected to benefit from increased HSP expression.

In certain embodiments of the methods disclosed herein, the condition being treated is CVD such as myocardial ischemia or MI. Myocardial ischemia is one of the most common causes of heart failure, with subsequent progression to MI. Even transient ischemia can lead to myocardial necrosis and apoptosis. Myocardial reperfusion strategies aim to reduce morbidity and mortality by restoring tissue oxygenation, but may in fact result in further cellular damage due to mitochondrial generation of reactive oxygen species. This phenomenon is known as I/R injury (Murphy Physiol Rev 88:581 (2008)). It is now recognized that HSPs play an important role in protecting against I/R. In those embodiments where CVD is being treated, the target site may be located in or around the heart or a component of the circulatory system. For example, the target site may be located in or around a coronary artery. In these embodiments, thermal ablation may target the heart or a blood vessel, or one or more nerves proximate to the heart or a blood vessel. In those embodiments that target CVD, thermal ablation may be carried out in conjunction with percutaneous coronary intervention (PCI) or angioplasty.

In certain embodiments of the methods disclosed herein, the condition being treated is PAD. For example, the methods may be used to treat low extremity vascular arterial beds that have restricted blood flow due to atherosclerosis, including partial vessel occlusions that generate ischemic conditions in the surround tissues. Induction of HSP expression may salvage tissue damage related to oxygen deprivation and intervention reoxygenation-related cell death. In those embodiments where PAD is being treated, the target site may be located in or around a peripheral blood vessel such as a peripheral artery, or in or around a nerve proximate to a peripheral blood vessel. In those embodiments that target PAD, thermal ablation may be carried out in conjunction with PCI.

In certain embodiments of the methods disclosed herein, the condition being treated is one where structural and functional preservation of proteins may enhance cell survival. These conditions include, for example, neurodegeneration, trauma, and stroke.

In certain embodiments of the methods disclosed herein, the condition being treated is a condition associated with a transplanted graft, including for example a kidney graft. In these embodiments, the methods may be used to treat graft-versus-host disease. HSP70 expression has been shown previously to improve tissue survival in animals undergoing ischemia of transplanted kidneys (Perdrizet Transplant Proc 25:1670 (1993)). In those embodiments where conditions associated with transplanted grafts are being treated, the target site may be located in or around an artery feeding the transplanted graft such as a renal artery, or in or around a nerve proximate to the artery.

Treatment of a condition for which increased HSP expression is expected to be beneficial may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A target site may be located in any target tissue that can be subjected to thermal ablation. As disclosed herein, thermal ablation of renal efferent nerves was shown to increase HSP expression at renal target sites. Thermal ablation is likewise expected to result in a similar increase in HSP expression levels in other tissue types. In certain embodiments of the methods disclosed herein, the target site may depend on the specific condition being treated. In certain embodiments, a target site is located in a target tissue that is currently experiencing an HSP expression pattern or another characteristic associated with a condition for which increased HSP expression is expected to be beneficial. In other embodiments, the target tissue has previously experienced such expression patterns or other characteristics, or has been deemed at risk for experiencing such expression patterns or other characteristics. In certain embodiments, a target site may exhibit decreased levels of one or more HSPs. In certain embodiments, the target site may be located in a target tissue that is associated with the condition being treated or symptoms thereof. For example, where the condition being treated is cancer, the target site may be located at or near a tumor site. Similarly, where the condition being treated is atherosclerosis, the target site may be located at or near a vessel exhibiting atherosclerotic plaque formation.

The methods disclosed herein may use any thermal ablation technique known in the art, including the use of monopolar or bipolar RF energy, microwave energy, laser light or optical energy, ultrasound energy (e.g., intravascularly delivered ultrasound, extracorporeal ultrasound, HIFU), magnetic energy, direct heat energy, cryotherapeutic energy, or a combination thereof. Alternatively or in addition to these techniques, the methods may utilize one or more non-thermal neuromodulatory techniques. For example, the methods may utilize sympathetic nervous system (SNS) denervation by removal of target nerves, injection of target nerves with a destructive drug or pharmaceutical compound, or treatment of the target nerves with non-thermal energy modalities. In certain embodiments, the magnitude or duration of the increase in HSP expression may vary depending on the specific technique being used.

Thermal ablation may be carried out using any ablation device known in the art. In certain embodiments, ablation may be carried out using a device that is in direct or close contact with a target site. In certain of these embodiments, the ablation device may access the target site via a minimally invasive route, for example via an intravascular pathway such as a femoral, brachial, or radial point of entry. In these embodiments, the ablation device and related components may have size, flexibility, torque-ability, kink resistance, or other characteristics suitable for accessing narrow or difficult to reach portions of vessels. In other embodiments, the target site may be accessed using an invasive direct access technique. In certain embodiments, the device may be used externally, i.e., without direct or close contact to the target site.

In certain embodiments, an ablation device for use in the methods disclosed herein may combine two or more energy modalities. The device may include both a hyperthermic source of ablative energy and a hypothermic source, making it capable of, for example, performing both RF ablation and cryoablation. The distal end of the treatment device may be straight (for example, a focal catheter), expandable (for example, an expanding mesh or cryoballoon), or have any other configuration (e.g., a helical or spiral coil). Additionally or alternatively, the treatment device may be configured to carry out one or more non-thermal neuromodulatory techniques. For example, the device may comprise a means for diffusing a drug or pharmaceutical compound onto the target treatment area (for example, a distal spray nozzle).

In those embodiments of the methods disclosed herein that include a step of measuring HSP expression levels before or after thermal ablation, such measurement can be carried out using any method known in the art. For example, the measurement can utilize one or more capture or detection agents that specifically bind HSP, such as an antibody or epitope-binding portion thereof, an HSP receptor or a portion thereof, or a nucleic acid complementary to all or a portion of the HSP mRNA sequence. FIG. 1 illustrates the use of a labeled antibody to bind and detect an HSP expressed on the artery wall (upper panel) or a secreted HSP (middle panel). In other examples, measurement of HSP expression may utilize a detection agent that has a functional interaction with HSP. For example, the detection agent may be a substrate for an HSP or an enzyme or catalytic antibody for which HSP is a substrate. FIG. 1 illustrates the use of a detection agent (represented by scissors) that functions to cleave off a portion of an HSP. In still other examples, measurement of HSP may be carried out using imaging/spectroscopy techniques that allow HSP levels to be assessed in a non-invasive manner or by tissue sampling.

Capture or detection agents for use detecting and measuring HSP expression may be in solution, or they may be immobilized on a surface such as a bead, resin, or one or more surfaces of an ablation or other treatment device, a component thereof, or a separate capture device. Examples of suitable resins include, for example, hydrophobic resins, cation/anion exchange resins (e.g., carboxymethyl, sulfopropyl/diethylamine), immobilized metal affinity chromatography (IMAC) resins, and polar chromatographic resins (e.g., silica gel). In those embodiments wherein capture or detection agents are immobilized on one or more surfaces of a treatment device, a component thereof, or a separate capture device, the capture or detection agents may be on the outside of the device, i.e., in direct contact with arterial blood or the artery wall. In other embodiments, the capture or detection agents may be on an internal surface, such as the interior of a catheter or a capture compartment.

In certain embodiments, binding of HSP to a capture agent and/or interaction of HSP with a detection agent results in a quantifiable signal. This quantifiable signal may be, for example, a colorimetric, fluorescent, heat, energy, or electric signal. In certain embodiments, this signal may be transduced to an external visual output device (see, e.g., FIG. 2). In certain embodiments, a capture or detection agent may be labeled, such as for example with an enzymatic or radioactive label. A capture or detection agent may be a binding substrate for a secondary capture agent, such as a labeled antibody.

Figure 3:
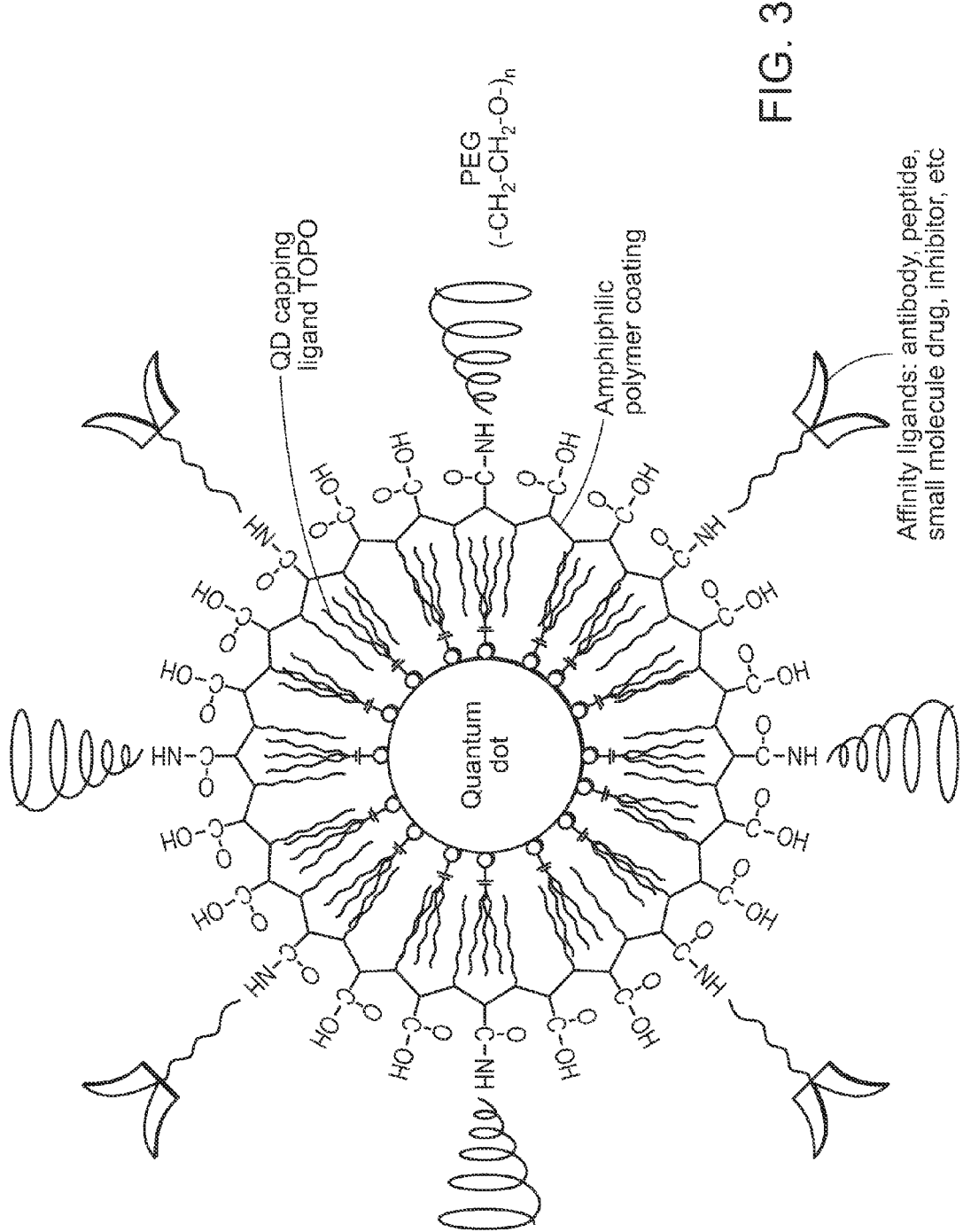
FIG. 3: Quantum dot system for generation of a detectable signal following binding of an HSP to an affinity ligand capture agent.
Figure 4:
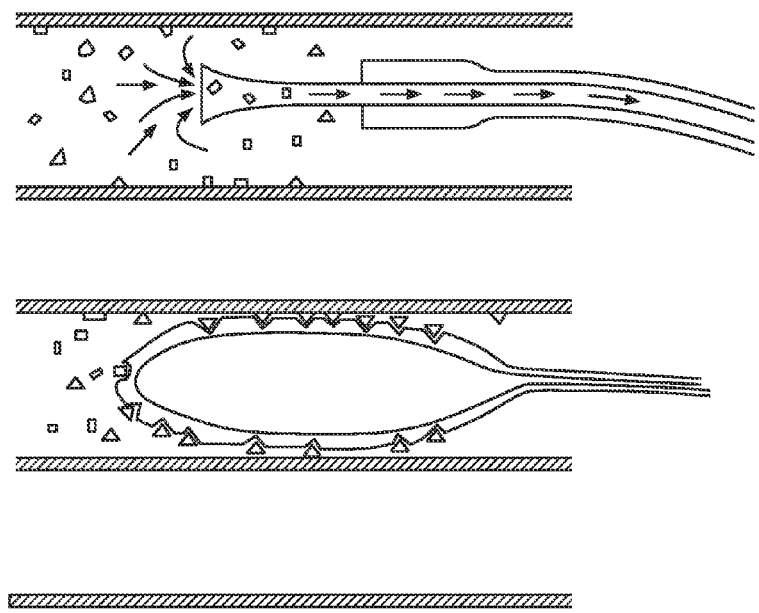
FIG. 4: Illustrative HSP capture methods: removal from ablation site and sequestration in a capture compartment for analysis in vivo or ex vivo (upper panel), balloon-based/semi-permeable filtering device with antibody based/immuno-electrochemical technology embedded within for capture and analysis in vivo or ex vivo (lower panel).

In certain embodiments, binding of HSP to a capture agent results in a signal that can be transduced to an external monitoring device. For example, binding of HSP to a capture or detection agent may be detected using a high sensitivity fluorescence technique such as a resonance energy transfer method (e.g., Forster resonance energy transfer, bioluminescence resonance energy transfer, or surface plasmon resonance energy transfer). FIG. 3 illustrates a quantum dot embodiment for generating a signal based on binding of HSP to an affinity ligand capture agent (e.g., an antibody, peptide, small molecule drug, or inhibitor). Quantum dots are nanometer sized semiconductor crystals that fluoresce when excited with the proper frequency of light (see, e.g., Xing Nat Protoc 2:1152 (2007)). The emitted light is tuned by the size of the nanocrystal, and excitation frequencies range from near IR to UV. Dynamic visualization through skin has been demonstrated in animals using near IR radiation.

In certain embodiments of the methods disclosed herein, determination of baseline and/or post-ablation HSP expression or activity is carried out using any immunoassay-based method. For example, HSP levels may be determined using an electrochemical immunosensor (see, e.g., FIG. 13), which provides concentration-dependent signaling (see, e.g., Centi Bioanalysis 1:1271 (2009); Rusling Analyst 135:2496 (2010)). Antibodies for use in an immunoassay-based determination of HSP level or activity may be labeled or unlabeled.

In certain embodiments, determination of baseline and/or post-ablation HSP level or activity takes place in vivo. In these embodiments, the determination may be carried out using the same device that is used to carry out ablation, or a component attached to the ablation device. Alternatively, determination of HSP level or activity may be carried out using a separate device. In certain of these embodiments, the separate device is delivered to the ablation site via the same catheter used to deliver the treatment device. In other embodiments, determination of baseline and/or post-ablation HSP level or activity takes place ex vivo.

In certain embodiments, the interaction between HSP and a capture or detection agent takes place at or near the ablation site. In certain of these embodiments, HSP binds to a capture or detection agent in the bloodstream or at the surface of the arterial wall. In these embodiments, the capture or detection agent may be in solution (i.e., in the bloodstream) or immobilized to a surface that is contact with the bloodstream and/or arterial wall. For example, a device or component thereof in which a capture or detection agent is integrated may be a balloon coated with one or more detection molecules that inflates to touch the ablated artery wall (see, e.g., FIG. 4, lower panel). Captured biomarkers may be detected in vivo, or the balloon-based device may be removed for biomarker detection er vivo.

In other embodiments, the interaction between HSP and a capture or detection agent takes place away from the ablation site. For example, HSP may be removed from an ablation site and sequestered in a capture compartment (see, e.g., FIG. 4, upper panel). Removal from the ablation site may utilize one or more filters. For example, a first filter at the distal end of a capture compartment may be selected such that it allows passage of HSP into the capture compartment while preventing passage of other biomolecules. A second filter at a proximal end of the capture component may be selected such it prevents passage of HSP out of the capture compartment while allowing blood to flow out of the capture compartment. Through the use of one or more filters, HSP may be concentrated within the capture compartment. Alternatively or in addition to the use of filters, one or more additional steps may be taken to concentrate HSP in the capture compartment prior to or simultaneous with contacting of HSP with capture or target agents. For example, HSP may be concentrated using beads. In certain embodiments that utilize a capture compartment, HSP is contacted with capture or detection agents in the capture compartment while still in the body. Alternatively, the capture compartment may be removed from the body prior to contacting HSP with capture or detection agents.

In one embodiment of the methods disclosed herein, an RF ablation catheter is used as the treatment device. The RF ablation catheter is advanced directly to a target site such as the renal artery or a specific location within the renal artery via an intravascular pathway. In this embodiment, the RF ablation catheter comprises an elongate shaft having a distal end and a plurality of electrodes (as the treatment elements) coupled thereto. An introducer sheath may be used to facilitate advancement of the device to the target site. Further, image guidance, such as computed tomography (CT) fluoroscopy, intravascular ultrasound (IVUS), optical coherence tomography (OCT), or other suitable guidance modality, or combinations thereof, may be used to aid the clinician's manipulation. In certain embodiments, image guidance components (for example, IVUS or OCT) may be incorporated into the treatment device itself. Once the treatment device is adequately positioned in contact or close proximity to the target site, the device is activated and RF energy is applied from the one or more electrodes, effectively ablating the arterial tissue. Ablation continues for a predetermined amount of time, or until visualization of the treatment area shows sufficient ablation. The RF ablation catheter is then removed from the patient. In those embodiments wherein HSP levels are measured subsequent to ablation, a sample for HSP expression measurement may be obtained using the device or a component attached thereto prior to removal. In other embodiments, an introducer sheath may be left in place following catheter removal, and a sampling device may be advanced to the target site.

Figure 14:
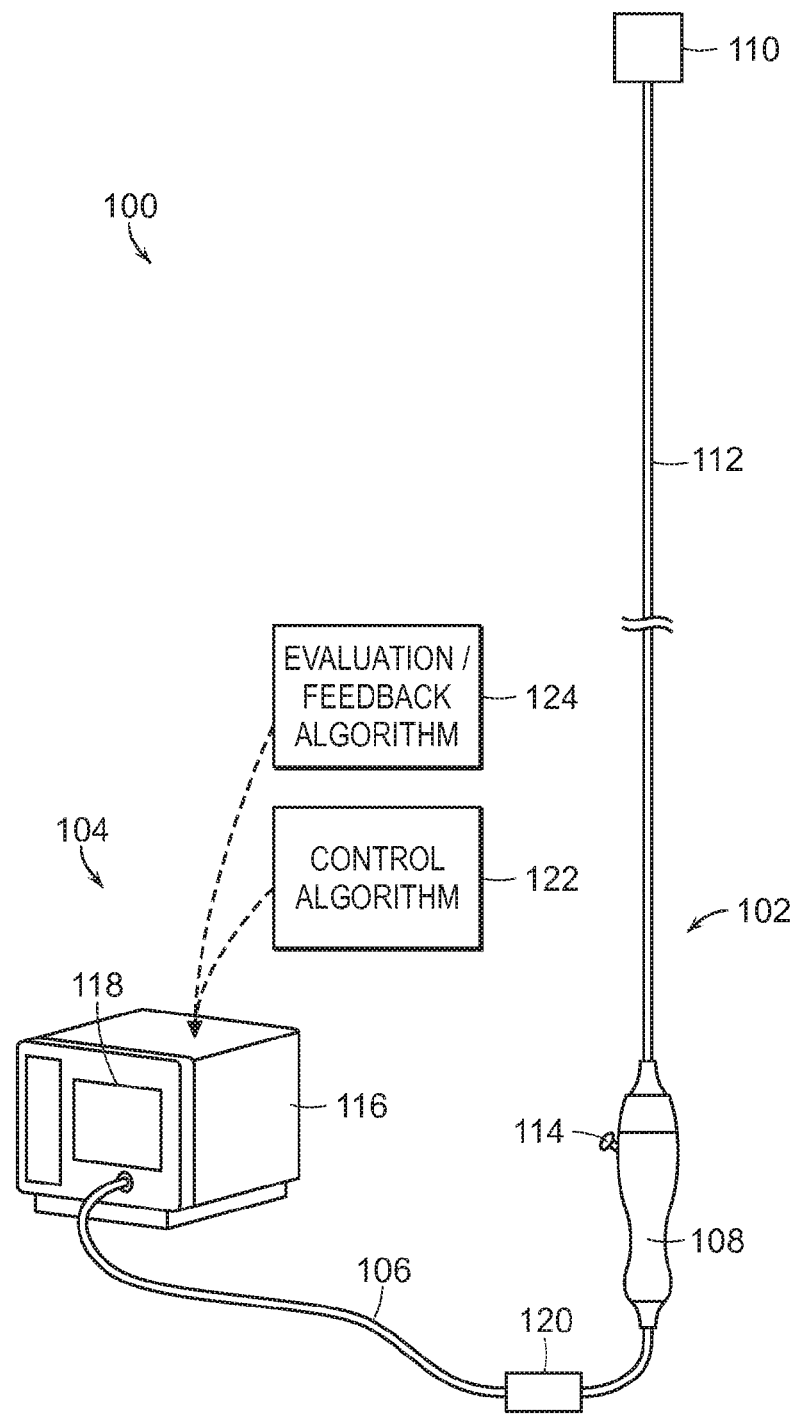
FIG. 14: Embodiments of a system for carrying out the methods disclosed herein.

In one embodiment, the methods disclosed herein utilize a neuromodulation system as set forth in FIG. 14. This neuromodulation system 100 ("system 100") can include a treatment device 102 for carrying out ablation, an energy source or console 104 (e.g., an RF energy generator, a cryotherapy console, etc.), and a cable 106 extending between the treatment device 102 and the console 104. The treatment device 102 can include a handle 108, a therapeutic element 110, and an elongated shaft 112 extending between the handle 108 and the therapeutic element 110. The shaft 112 can be configured to locate the therapeutic element 110 intravascularly or intraluminally at a treatment location, and the therapeutic element 110 can be configured to provide or support therapeutically-effective neuromodulation at the treatment location. In certain embodiments, the shaft 112 and the therapeutic element 110 can be 3, 4, 5, 6, or 7 French or another suitable size. Furthermore, the shaft 112 and the therapeutic element 110 can be partially or fully radiopaque and/or can include radiopaque markers corresponding to measurements, e.g., every 5 cm. In certain embodiments, the treatment device comprises an optional monitoring or sampling component for evaluating changes in HSP expression.

Intravascular delivery can include percutaneously inserting a guide wire (not shown) within the vasculature and moving the shaft 112 and the therapeutic element 110 along the guide wire until the therapeutic element 110 reaches the treatment location. For example, the shaft 112 and the therapeutic element 110 can include a guide-wire lumen (not shown) configured to receive the guide wire in an over-the-wire (OTW) or rapid-exchange configuration (RX). Other body lumens (e.g., ducts or internal chambers) can be treated, for example, by non-percutaneously passing the shaft 112 and therapeutic element 110 through externally accessible passages of the body or other suitable methods. In some embodiments, a distal end of the therapeutic element 110 can terminate in an atraumatic rounded tip or cap (not shown). The treatment device 102 can also be a steerable or non-steerable catheter device configured for use without a guide wire.

The therapeutic element 110 can have a single state or configuration, or it can be convertible between a plurality of states or configurations. For example, the therapeutic element 110 can be configured to be delivered to the treatment location in a delivery state and to provide or support therapeutically-effective neuromodulation in a deployed state. In these and other embodiments, the therapeutic element 110 can have different sizes and/or shapes in the delivery and deployed states. For example, the therapeutic element 110 can have a low-profile configuration in the delivery state and an expanded configuration in the deployed state. In another example, the therapeutic element 110 can be configured to deflect into contact with a vessel wall in a delivery state. The therapeutic element 110 can be converted (e.g., placed or transformed) between the delivery and deployed states via remote actuation, e.g., using an actuator 114 of the handle 108. The actuator 114 can include a knob, a pin, a lever, a button, a dial, or another suitable control component. In other embodiments, the therapeutic element 110 can be transformed between the delivery and deployed states using other suitable mechanisms or techniques.

In some embodiments, the therapeutic element 110 can include an elongated member (not shown) that can be configured to curve (e.g., arch) in the deployed state, e.g., in response to movement of the actuator 114. For example, the elongated member can be at least partially helical/spiral in the deployed state. In other embodiments, the therapeutic element 110 can include a balloon (not shown) that can be configured to be at least partially inflated in the deployed state. An elongated member, for example, can be well suited for carrying one or more electrodes or transducers and for delivering electrode-based or transducer-based treatment. A balloon, for example, can be well suited for containing refrigerant (e.g., during or shortly after liquid-to-gas phase change) and for delivering cryotherapeutic treatment. In some embodiments, the therapeutic element 110 can be configured for intravascular, transvascular, intraluminal, and/or transluminal delivery of chemicals. For example, the therapeutic element 110 can include one or more openings (not shown), and chemicals (e.g., drugs or other agents) can be deliverable through the openings. For transvascular and transluminal delivery, the therapeutic element 110 can include one or more needles (not shown) (e.g., retractable needles) and the openings can be at end portions of the needles.

The console 104 is configured to control, monitor, supply, or otherwise support operation of the treatment device 102. In other embodiments, the treatment device 102 can be self-contained and/or otherwise configured for operation without connection to the console 104. As shown in FIG. 14, the console 104 can include a primary housing 116 having a display 118. The system 100 can include a control device 120 along the cable 106 configured to initiate, terminate, and/or adjust operation of the treatment device 102 directly and/or via the console 104. In other embodiments, the system 100 can include another suitable control mechanism. For example, the control device 120 can be incorporated into the handle 108. The console 104 can be configured to execute an automated control algorithm 122 and/or to receive control instructions from an operator. Furthermore, the console 104 can be configured to provide feedback to an operator before, during, and/or after a treatment procedure via the display 118 and/or an evaluation/feedback algorithm 124. In some embodiments, the console 104 can include a processing device (not shown) having processing circuitry, e.g., a microprocessor. The processing device can be configured to execute stored instructions relating to the control algorithm 122 and/or the evaluation/feedback algorithm 124. Furthermore, the console 104 can be configured to communicate with the treatment device 102, e.g., via the cable 106. For example, the therapeutic element 110 of the treatment device 102 can include a sensor (not shown) (e.g., a recording electrode, a temperature sensor, a pressure sensor, or a flow rate sensor) and a sensor lead (not shown) (e.g., an electrical lead or a pressure lead) configured to carry a signal from the sensor to the handle 108. The cable 106 can be configured to carry the signal from the handle 108 to the console 104.

The console 104 can have different configurations depending on the treatment modality of the treatment device 102. For example, when the treatment device 102 is configured for electrode-based or transducer-based treatment, the console 104 can include an energy generator (not shown) configured to generate RF energy, pulsed RF energy, microwave energy, optical energy, focused ultrasound energy (e.g., HIFU), direct heat energy, or another suitable type of energy. In some embodiments, the console 104 can include an RF generator operably coupled to one or more electrodes (not shown) of the therapeutic element 110. When the treatment device 102 is configured for cryotherapeutic treatment, the console 104 can include a refrigerant reservoir (not shown) and can be configured to supply the treatment device 102 with refrigerant, e.g., pressurized refrigerant in liquid or substantially liquid phase. Similarly, when the treatment device 102 is configured for chemical-based treatment, the console 104 can include a chemical reservoir (not shown) and can be configured to supply the treatment device 102 with the chemical. In certain embodiments, the therapeutic assembly may further include one or more thermoelectric devices (such as a Peltier device) for the application of heat or cold therapy. Any energy modality can either be used alone or in combination with other energy modalities. In some embodiments, the treatment device 102 can include an adapter (not shown) (e.g., a luer lock) configured to be operably coupled to a syringe (not shown). The adapter can be fluidly connected to a lumen (not shown) of the treatment device 102, and the syringe can be used, for example, to manually deliver one or more chemicals to the treatment location, to withdraw material from the treatment location, to inflate a balloon (not shown) of the therapeutic element 110, to deflate a balloon of the therapeutic element 110, or for another suitable purpose. In other embodiments, the console 104 can have other suitable configurations.

Upon delivery to a target site, the therapeutic assembly may be further configured to be deployed into a treatment state or arrangement for delivering energy at the treatment site. In some embodiments, the therapeutic assembly may be placed or transformed into the deployed state or arrangement via remote actuation, for example, via an actuator, such as a knob, pin, or lever carried by the handle. In other embodiments, however, the therapeutic assembly may be transformed between the delivery and deployed states using other suitable mechanisms or techniques. The monitoring system can provide feedback of parameters such as nerve activity to verify that the treatment assembly provided therapeutically effective treatment.

In the deployed state, the therapeutic assembly can be configured to contact an inner wall of a vessel and to carry out ablation or a series of ablations without the need for repositioning. For example, the therapeutic element can be configured to create a single lesion or a series of lesions, e.g., overlapping or non-overlapping. In some embodiments, the lesion or pattern of lesions can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the therapeutic element can be configured cause a partially-circumferential lesion or a fully-circumferential lesion at a single longitudinal segment or zone of the vessel.

The proximal end of the therapeutic assembly is carried by or affixed to the distal portion of the elongate shaft. A distal end of the therapeutic assembly may terminate with, for example, a rounded tip or cap. Alternatively, the distal end of the therapeutic assembly may be configured to engage another element of the system or treatment device.

For example, the distal end of the therapeutic assembly may define a passageway for engaging a guide wire (not shown) for the delivery of the treatment device using over-the-wire (OTW) or rapid exchange (RX) techniques. If the treatment device and the sampling component are part of a single intervention device, the intervention device may include one or more filters or testing media for in-system analysis of sample cells.

The monitoring system may include one or more energy sources (for example, a coolant reservoir and/or an RF generator), which may be housed in a console or used as a stand-alone energy source. The console or energy source is configured to generate a selected form and magnitude of energy for delivery to the target treatment site via the therapeutic assembly. A control mechanism such as a foot pedal may be connected to the console to allow the operator to initiate, terminate, and optionally to adjust various operational characteristics of the energy generator, including, but not limited to, power delivery. The system may also include a remote control device (not shown) that can be positioned in a sterile field and operably coupled to the therapeutic assembly. In other embodiments, the remote control device is configured to allow for selective activation of the therapeutic assembly. In other embodiments, the remote control device may be built into the handle assembly. The energy source can be configured to deliver the treatment energy via an automated control algorithm and/or under the control of the clinician. In addition, the energy source or console may include one or more evaluation or feedback algorithms to provide feedback to the clinician before, during, and/or after therapy. The feedback can be based on output from the monitoring system.

The energy source can further include a device or monitor that may include processing circuitry, such as one or more microprocessors, and a display. The processing circuitry can be configured to execute stored instructions relating to the control algorithm. The energy source may be configured to communicate with the treatment device to control the treatment assembly and/or to send signals to or receive signals from the monitoring system. The display may be configured to provide indications of power levels or sensor data, such as audio, visual, or other indications, or may be configured to communicate the information to another device. For example, the console may also be operably coupled to a catheter lab screen or system for displaying treatment information, including for example nerve activity before and after treatment, effects of ablation or temperature therapy, lesion location, lesion size, etc.

The distal end of one embodiment of a treatment device includes a distal electrode which is used to apply energy to the target cells (for example, RF energy or ultrasound energy), although a plurality of electrodes can instead be used. Alternatively or additionally, the distal end can include a light emitter such as a laser or LED diode, or a microwave antenna (not shown). The distal end can further include a radiopaque marker band for positioning the device.

The distal end of another embodiment of a treatment device includes a cryoballoon, which is used to cool (remove energy from) the target cells. In this embodiment, the distal end of the treatment device includes an inner balloon and an outer balloon, which may help prevent coolant leaks from the cryoballoon. If additional energy modalities are used, the cryoballoon may include one or more electrodes, antennas, or laser diodes, or LED diodes (not shown). The distal end may further include a radiopaque marker band for positioning the device.

One of ordinary skill in the art will recognize that the various embodiments described herein can be combined. The following examples are provided to better illustrate the disclosed technology and are not to be interpreted as limiting the scope of the technology. To the extent that specific materials are mentioned, it is merely for purposes of illustration and is not intended to limit the technology. One skilled in the art may develop equivalent means or reactants without the exercise of inventive capacity and without departing from the scope of the technology. It will be understood that many variations can be made in the procedures herein described while still remaining within the bounds of the present technology. It is the intention of the inventors that such variations are included within the scope of the technology.

EXAMPLES

Example 1

Effect of RF Ablation and SNS Denervation on HSP Levels

Animals were broken into three groups of three animals each: naïve (no treatment), sham (catheterized but not ablated), and treated (subject to ablation at 65° C. and 90 seconds using a spiral ablation catheter device). Left and right renal arteries and surrounding tissue samples were obtained by sampling tissue in the area of ablation at 10 minutes ("day 0"), 7 days, or 24 hours post-treatment. Slices from the center of ablation sites were removed for histopathological analysis, and the ablation sites were cleaned up by removing any non-ablated tissue and pooled. Tissue was maintained during the dissection process using RNALater® solution.

Pooled tissue samples were weighed and mixed under frozen conditions, and then added to round-bottomed tubes containing 2× stainless steel beads (5 mm diameter) at room temperature. 900 μL QIAzol lysis reagent was added to each tube, and the tissue was macerated using the TissueLyser II Adaptor Set with disruption at 30 Hz (3×2 minutes) to release RNA. An additional 300 μL of lysis buffer was added to each tube, and the disruption cycle was repeated (1×2 minutes at 30 Hz). Lysates were transferred to new Eppendorf tubes for mRNA isolation.

120 μl gDNA Eliminator Solution was added to each lysate sample, and tubes were shaken vigorously for 15 seconds. 180 μL of chloroform was added, and tubes were again shaken vigorously for 15 seconds. After 2-3 minutes at room temperature, tubes containing homogenate were centrifuged at 12,000×g for 15 minutes at 4° C. The centrifuge was warmed to room temperature, and the upper aqueous phase was transferred to a new Eppendorf tube. An equal volume of 70% ethanol was added to each tube with thorough mixing, and 700 μL of each sample was transferred to an RNeasy Mini spin column in a 2 mL collection tube. Samples were centrifuged for 15 seconds at >8000×g (>10,000 rpm) at room temperature and flow-thru was discarded. The ethanol mixing and RNeasy centrifugation steps were repeated until all sample was used up. 700 μL of Buffer RWT was added to each spin column, followed by centrifugation for 15 seconds at >8,000×g (>10,000 rpm) to wash the membrane. Flow-thru was discarded, and 500 μL Buffer RPE was added each spin column, followed by centrifugation for 15 seconds at >8,000×g (>10,000 rpm). Flow thru was discarded, and 500 μl Buffer RPE was again added to each spin column, followed by centrifugation for 2 minutes at >8,000×g (>10,000 rpm) to wash the membrane. RNeasy spin columns were placed in a new 2 mL collection tube and centrifuged at full speed for 1 minute. The spin column was placed in a new 1.5 mL collection tube, 50 μL RNase free water was added directly to the spin column membrane, and RNA eluted was eluted by centrifugation for 1 minute at >8,000×g (>10,000 rpm). This step was repeated using another 50 μL of RNase free water. To ensure significance, A260 readings were verified to be greater than 0.15. An absorbance of 1 unit at 260 nm corresponds to 44 μg of mRNA per mL (A260=1=44 μg/mL) at neutral pH.

ABI High Capacity cDNA kits were used to convert mRNA to cDNA for quantitative real-time PCR (qPCR). PCR was performed in optical 384-well plates, freshly prepared on the Eppendorf epMotion liquid handler. Final reaction volume was 20 μL (4 μL Taqman Assay+mixture of 6 μL cDNA (3 ng)+10 μL Universal Master Mix with UNG). Assays were performed to include +RT (reverse transcriptase) samples and, when appropriate, a −RT control. Endogenous controls (×2) were run in triplicate and animal samples were run only once for screening purposes. The real-time PCR protocol included an initial step of 50° C. (2 minutes) to activate the DNA polymerase, denaturation by a hot start at 95° C. for 10 minutes, and 40 cycles of a two step program (denaturation at 95° C. for 15 seconds for primer annealing/extension at 60° C. for 1 minute). Fluorescence data was collected at 60° C. Fluorescence was quantified with the ABI PRISM 7900HT, and the resultant data was analyzed using SDS RQ Manager (1.2.1) Software (Sequence Detection System Software, Applied Biosystems). Each biomarker was checked, and threshold and baseline was adjusted to produce (in Δ Rn versus Cycle) an amplification curve of the type suggested by Applied Biosystems in their "Relative Quantification Using Comparative Ct Getting Started Guide." A calibrator was selected for calculation of the RQ (relative quantification). The calibrator was based on an average of 6× figures from the three naïve animals, left & right arteries, resulting in a numerical result of 1 for the naïve RQ. For calculation of the RQ for the standard deviation (SD) of the naïves, any other experimental animal was used as a calibrator (generally the first animal for Day 0 treated). RQ averages of animals (×3) in the same treatment group were calculated for each point and for each biomarker individually, and plotted in bar graphs.

Figure 5:
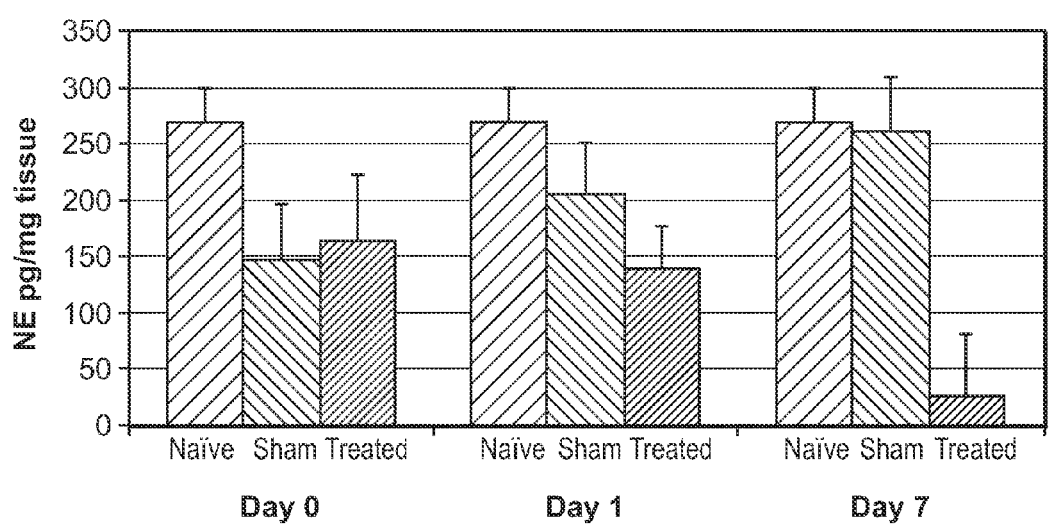
FIG. 5: Average kidney NE levels post-ablation.

Renal NE and dopamine (DBN) levels in naïve, sham, and test animals were evaluated at 10 minutes, 24 hours, and 7 days. Average kidney NE production post-ablation is shown in FIG. 5.

Figure 6:
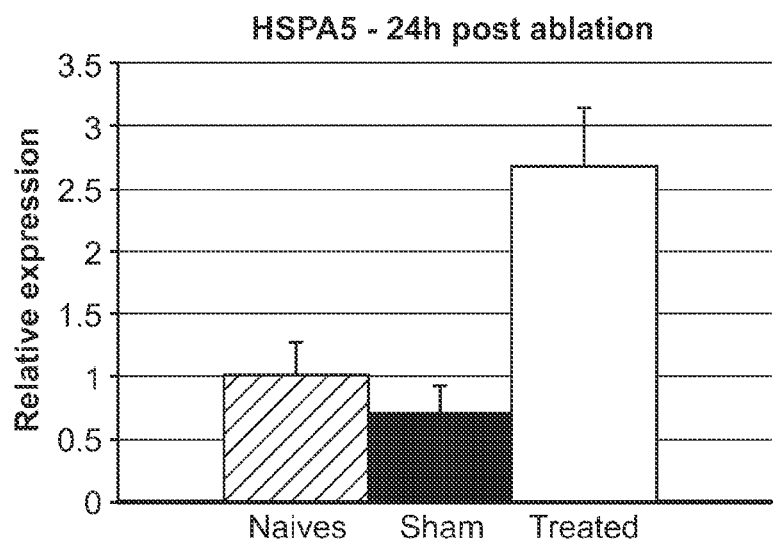
FIG. 6: Upregulation of HSPA5 24 hours post-ablation.
Figure 7:
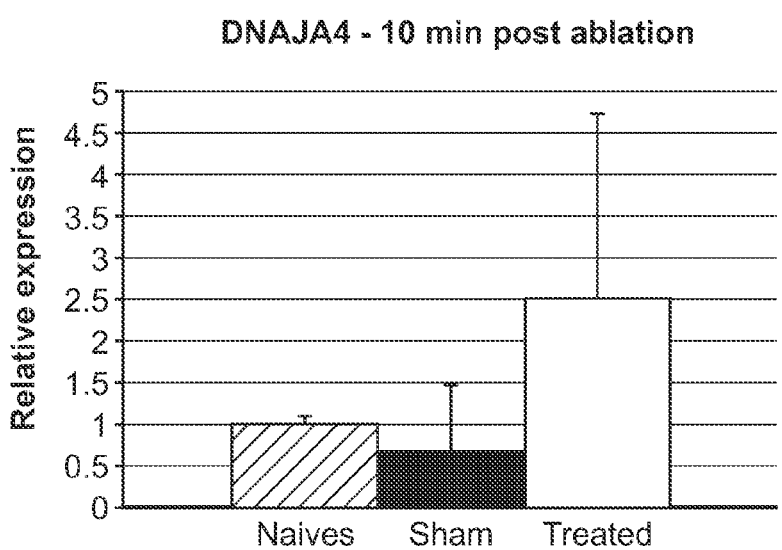
FIG. 7: Upregulation of DNAJA4 10 minutes post-ablation.
Figure 8:
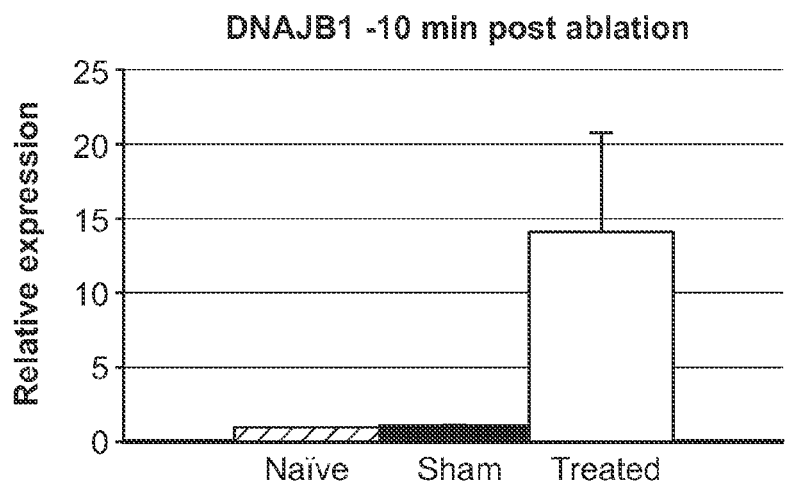
FIG. 8: Upregulation of DNAJB1 10 minutes post-ablation.
Figure 9A:
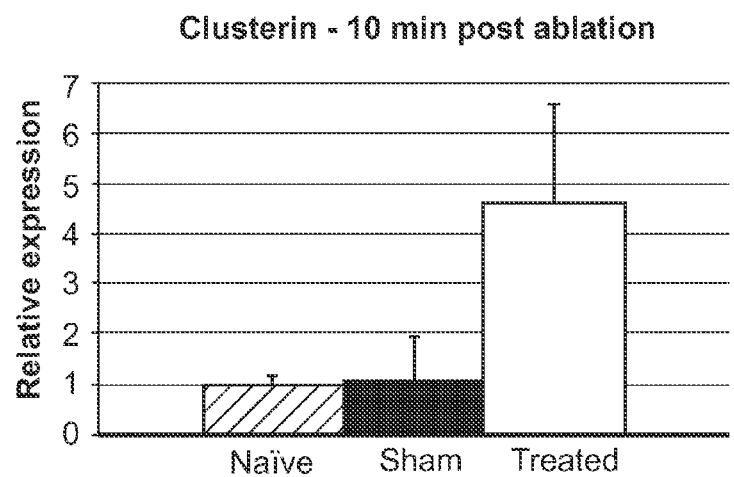
FIG. 9: Upregulation of CLU (A) 10 minutes and (B) 7 days post-ablation.
Figure 9B:
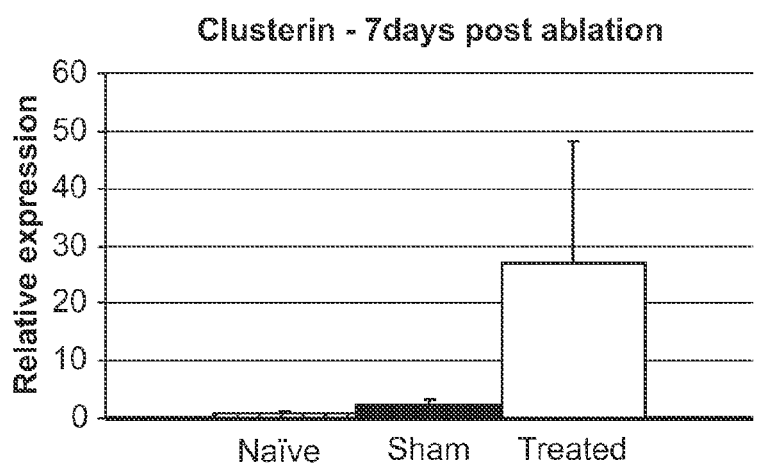
Figure 10:
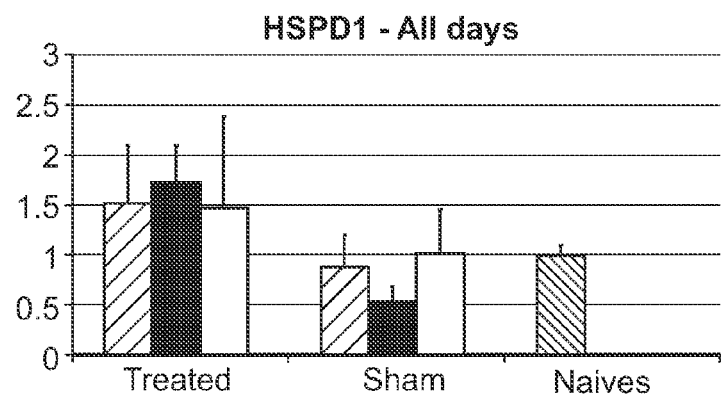
FIG. 10: Upregulation of HSPD1 10 minutes, 24 hours, and 7 days post-ablation.
Figure 11A:
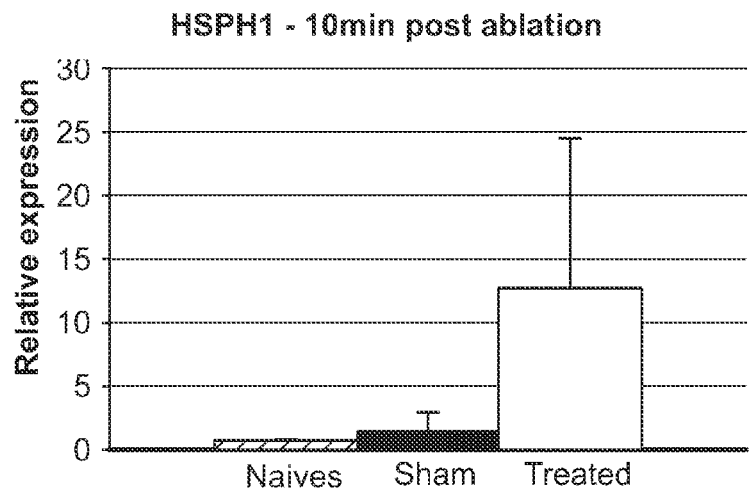
FIG. 11: Upregulation of HSPH1 (A) 10 minutes and (B) 24 hours post-ablation.
Figure 11B:
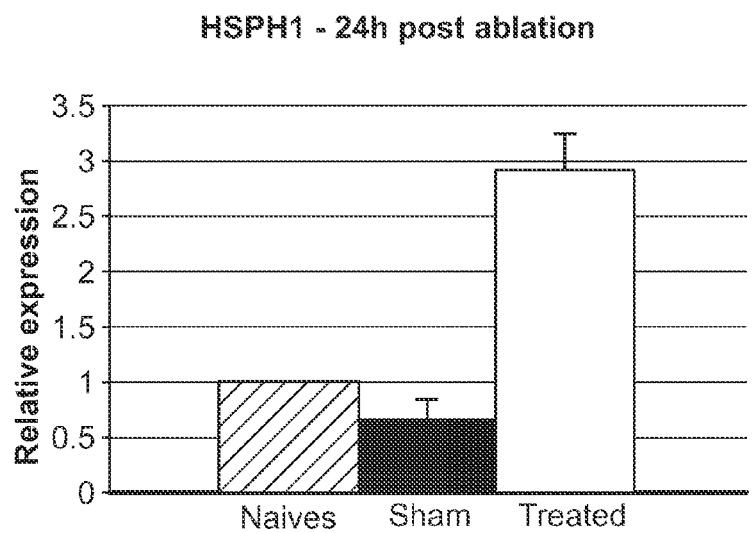
Figure 12A:
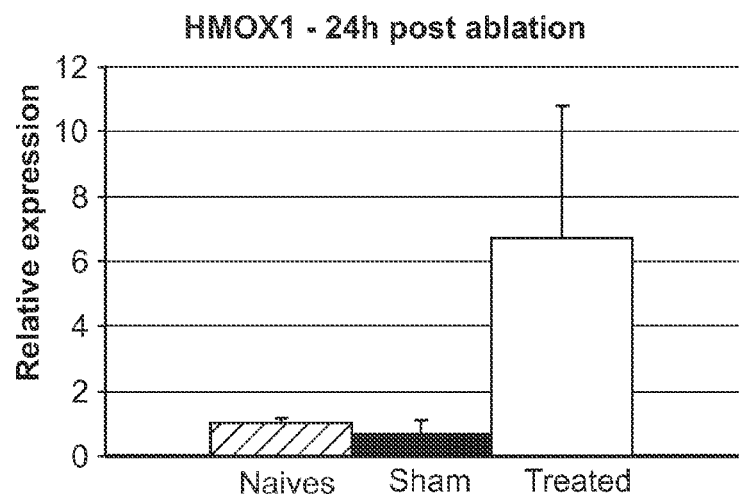
FIG. 12: Upregulation of HMOX1 (A) 24 hours and (B) 7 days post-ablation.
Figure 12B:
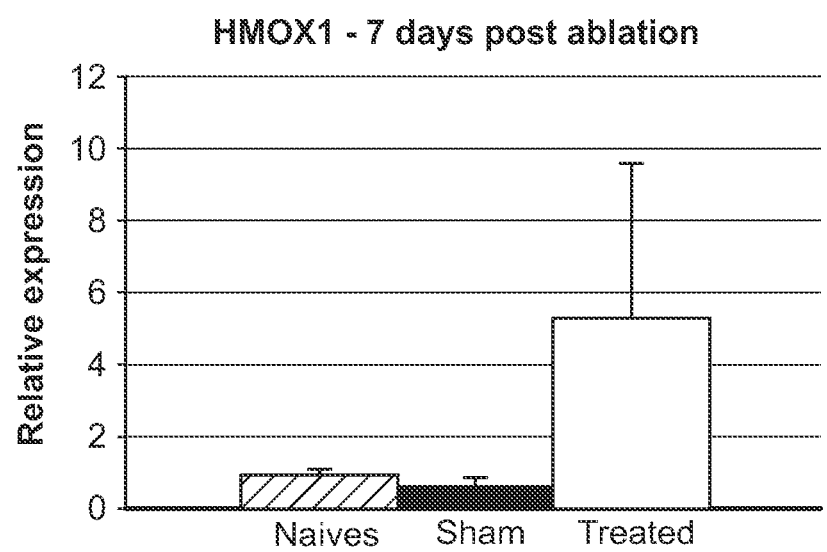
Figure 13:
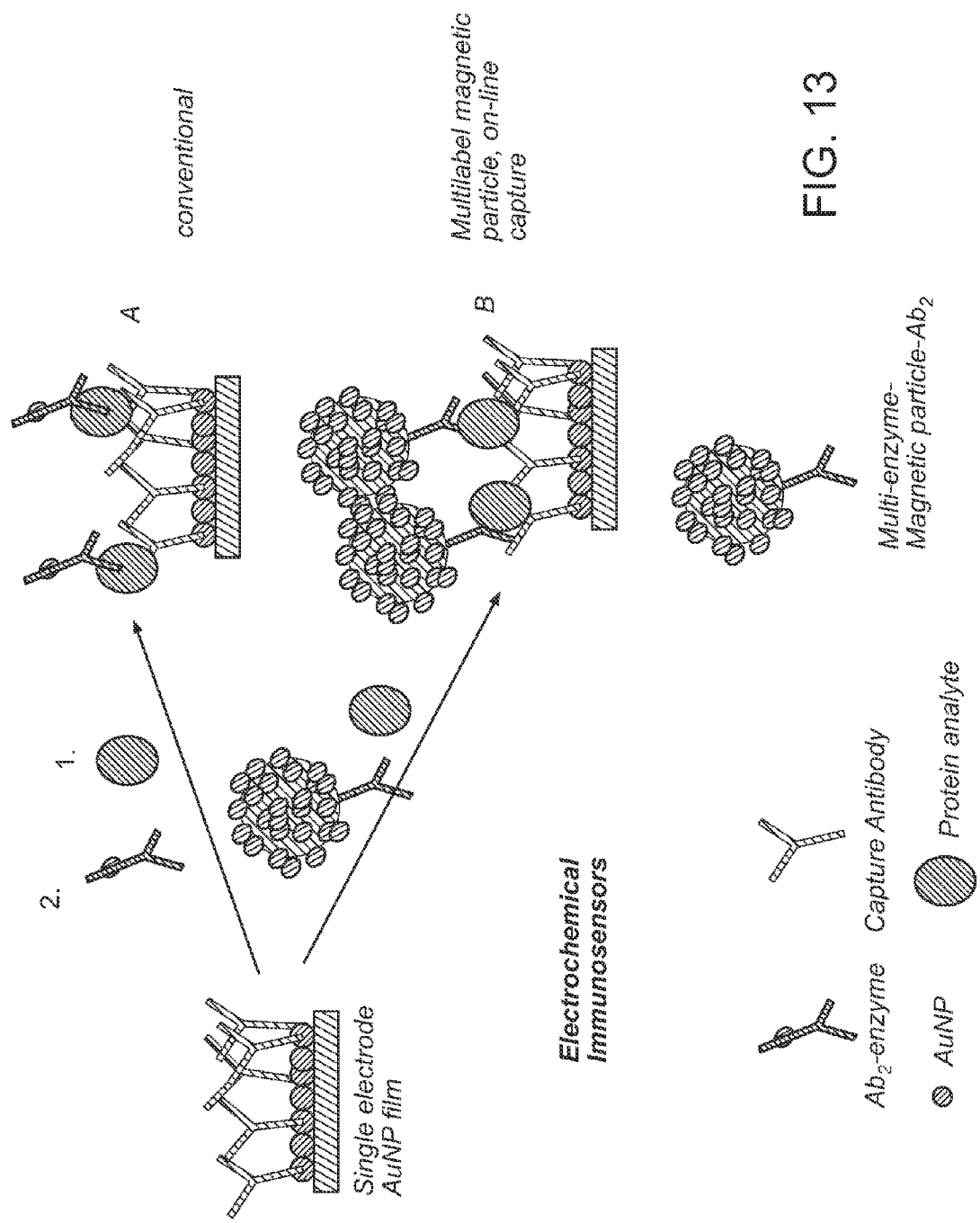
FIG. 13: Illustration of representative electrochemical immunosensor protocols.

The initial screen was carried out using 70 candidate biomarkers. HSPs exhibiting a significant increase in expression at 10 minutes post-ablation included DNAJA4 (FIG. 7), DNAJB1 (FIG. 8), HSPB1, CLU (FIG. 9A), HSPD1 (FIG. 10), and HSPH1 (FIG. 11A). HSPs exhibiting a significant increase in expression at 24 hours post-ablation included HSPD1 (FIG. 10), HSPH1 (FIG. 11B), HMOX1 (FIG. 12A), and HSPA5 (FIG. 6). HSPs exhibiting a significant increase in expression at 7 days post-ablation included HSPD1 (FIG. 10), HMOX1 (FIG. 12B), and CLU (FIG. 9B).

HSP expression in response to thermal ablation will be further evaluated in human vascular and neuronal cells (e.g., primary vascular cells such as Human Coronary Artery Endothelial Cells (HCAEC) or Human Coronary Artery Smooth Muscle Cells (HCASMC), neuronal cell lines). Expression can be evaluated by actually exposing cells to thermal ablation, or by simply exposing the cells to one or more conditions that mimic in vivo ablation (e.g., exposure to heat).

For experiments in which cells are exposed to heat, the cells are subjected to elevated temperatures (e.g., 65-95° C.) for various time intervals (e.g., 30-120 seconds) and allowed to recover at 37° C. HSP levels and/or activity are measured at the end of the testing phase and at various timepoints during the recovery phase (e.g., every 1-5 minutes).

Cell culture samples from various timepoints may be collected for HSP secretomics analysis to evaluate release of HSP into culture. Secretomics experiments may be performed using iTRAQ methodology (Wisniewski Arch Pathol Lab Med 132:1566 (2008)).

Treated and control cells from various timepoints are lysed and the cell contents are analyzed for changes in HSP level or activity. Changes in level or activity of one or more control proteins may also be measured. Analysis may be carried out using the iTRAQ methodology. For example, samples may be diluted (depending on their initial concentration), digested with trypsin, and iTRAQ labeled using 8-Plex reagent. The resultant complex protein digests are pooled together for MudPIT analysis. Each fraction is analyzed by LC-MS/MS, for example using an ABSciex 5500 QTRAP® mass spectrometer, for acquisition of mass spectroscopy data with the inclusion of iTRAQ quantitation data. Protein characterization for MS/MS and iTRAQ data can be performed using ABSciex ProteinPilot software v 4.0 (Paragon algorithm).

Additional Examples

1. A method for increasing HSP expression level at or near a target site in a subject, the method comprising performing a thermal ablation procedure at or near the target site, wherein the thermal ablation procedure results in an increase in the expression level of one or more HSPs at or near the target site.

2. A method for treating a condition for which increased HSP expression is expected to be beneficial in a subject, the method comprising performing a thermal ablation procedure, wherein the thermal ablation procedure results in an increase in HSP expression level, and wherein the increase in HSP expression level results in treatment of the condition.

3. The method of either of examples 1 or 2 wherein HSP expression level is increased within 30 minutes or less following the thermal ablation procedure.

4. The method of either of examples 1 or 2 wherein HSP expression level is increased within 10 minutes or less following the thermal ablation procedure.

5. The method of either of examples 1 or 2 wherein HSP expression level is increased at one or more timepoints selected from 10 minutes, 24 hours, and 7 days following the ablation procedure.

6. The method of either of examples 1 or 2 wherein the thermal ablation procedure is carried out using a modality selected from the group consisting of monopolar or bipolar radio frequency (RF) energy, microwave energy, laser or optical light energy, ultrasound energy, magnetic energy, direct heat energy, and cryotherapeutic energy.

7. The method of either of examples 1 or 2 wherein the target site is in a renal blood vessel of the human subject.

8. The method of example 7 wherein the thermal ablation procedure targets renal sympathetic nerves.

9. The method of example 2, wherein the condition is selected from the group consisting of CVD, PAD, trauma, stroke, diabetes, atherosclerosis, asthma, other chronic inflammatory conditions, cancer, neurodegeneration, and various neurological disorders 10. The method of either of examples 1 or 2 wherein the thermal ablation procedure results in an increase in expression of an HSP selected from the group consisting of HSPA5, DNAJA4, DNAJB1, CLU, HSPD1, HSPH1, HMOX1, and HSPB1.

11. A device for carrying out the method of any of examples 1-10.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for increasing a heat shock protein (HSP) expression level at or near a target site in a subject, the method comprising:
   determining a baseline HSP expression level for one or more HSPs at or near the target site in the subject;
   performing a thermal ablation procedure at or near the target site;
   determining a post-ablation HSP expression level for the one or more HSPs at or near the target site in the subject; and
   comparing the post-ablation HSP expression level to the baseline HSP expression level, wherein the thermal ablation procedure is classified as successful if the post-ablation HSP expression level is increased from the baseline HSP expression level.

2. The method of claim 1 wherein the post-ablation HSP expression level is at least two-fold higher that the baseline HSP expression level.

3. The method of claim 1 wherein the HSP expression level includes one or more of a HSP mRNA level, a HSP protein level, a level of secreted HSP protein and a level of HSP activity.

4. The method of claim 1, further comprising performing a second thermal ablation procedure if the post-ablation HSP expression level is not significantly increased from the baseline HSP expression level.

5. The method of claim 1 wherein determining a baseline HSP expression level and determining a post-ablation HSP expression level includes quantifying the HSP expression level in vivo.

6. The method of claim 1 wherein determining the baseline HSP expression level and the post-ablation HSP expression level includes acquiring HSP protein via an intravascularly positioned capture device.

7. The method of claim 1 wherein the post-ablation HSP expression level is at least about 50%, about 100%, or about 200% greater than the baseline HSP expression level.

8. A method for treating a condition for which increased HSP expression is expected to be beneficial in a subject, the method comprising:
   intravascularly positioning a catheter carrying an ablation assembly within a target blood vessel of the subject;
   target tissue proximate the target blood vessel via the ablation assembly to thermally ablate the target tissue, wherein thermal ablation of the target tissue results in an increase in a HSP expression level; and
   after delivering energy to the target tissue, quantifying the HSP expression level and comparing the HSP expression level to a pre-determined threshold expression level for the HSP,
   wherein the HSP expression level is beneficial in the treatment of the condition if the HSP expression level is greater than the pre-determined threshold expression level.

9. The method of claim 8 wherein, after delivering energy to the target tissue, the HSP expression level is increased at one or more timepoints selected from 10 minutes, 24 hours, and 7 days.

10. The method of claim 8 wherein delivering energy to target tissue comprises delivering energy selected from the group consisting of monopolar or bipolar radio frequency energy, microwave energy, laser or optical light energy, ultrasound energy, magnetic energy, direct heat energy, and cryotherapeutic energy.

11. The method of claim 8 wherein the target blood vessel is a renal blood vessel of the subject.

12. The method of claim 11 wherein delivering energy to target tissue comprises delivering energy to target renal sympathetic nerves.

13. The method of claim 8 wherein the condition is selected from the group consisting of cardiovascular disease, peripheral artery disease, trauma, stroke, diabetes, atherosclerosis, asthma, other chronic inflammatory conditions, cancer, neurodegeneration, and various neurological disorders.

14. The method of claim 8 wherein thermal ablation of the target tissue results in an increase in expression of a HSP selected from the group consisting of HSPA5, DNAJA4, DNAJB1, CLU, HSPD1, HSPH1, HMOX1, and HSPB1.

15. A method for treating a condition for which increased HSP expression is expected to be beneficial in a patient, the method comprising performing a thermal ablation procedure at a target site, wherein the target site is within a blood vessel of the patient, and wherein the thermal ablation procedure results in an increase in the expression level of one or more HSPs at a location remote to the target site.

16. The method of claim 15 wherein HSP protein is carried via the bloodstream to the remote location.

17. A method for treating a condition associated with an affected tissue for which increased HSP expression is expected to be beneficial in a human patient, the method comprising:
   intravascularly positioning a catheter carrying an ablation assembly within a target blood vessel proximate the affected tissue of the patient; and
   delivering energy through a wall of the target blood vessel to target tissue proximate the blood vessel via the ablation assembly to at least partially thermally ablate the target tissue, wherein thermal ablation of the target tissue results in an increase in a HSP expression level at or near the affected tissue in the patient,
   wherein the increase in the HSP expression level is at least partially beneficial in the treatment of the condition.

18. The method of claim 17 wherein the condition is myocardial ischemia or myocardial infarction, and wherein the target blood vessel is in or near the heart of the subject.

19. The method of claim 17 wherein the condition is peripheral artery disease, and wherein the target blood vessel is a peripheral artery.

20. The method of claim 17 wherein, after delivering energy to the target tissue, the method further comprises quantifying the HSP expression level and comparing the HSP expression level to a pre-determined threshold expression level for the HSP.

* * * * *